(12) United States Patent
Von Malmborg

(10) Patent No.: US 8,551,022 B2
(45) Date of Patent: *Oct. 8, 2013

(54) SENSOR GUIDE WIRE

(75) Inventor: Pär Von Malmborg, Uppsala (SE)

(73) Assignee: St. Jude Medical Systems AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/537,826

(22) Filed: Jun. 29, 2012

(65) Prior Publication Data

US 2013/0006122 A1    Jan. 3, 2013

Related U.S. Application Data

(63) Continuation of application No. 12/739,284, filed as application No. PCT/SE2008/051211 on Oct. 24, 2008, now Pat. No. 8,226,578.

(60) Provisional application No. 60/996,064, filed on Oct. 26, 2007.

(51) Int. Cl.
*A61M 25/00*    (2006.01)

(52) U.S. Cl.
USPC .......................................................... 600/585

(58) Field of Classification Search
USPC ...................... 600/433, 434, 585; 604/164.13
See application file for complete search history.

(56) References Cited

U.S. PATENT DOCUMENTS

| 6,061,588 | A | 5/2000 | Thornton et al. |
| 6,142,958 | A | 11/2000 | Hammarstrom et al. |
| 6,183,424 | B1 * | 2/2001 | Schwager ............ 600/585 |
| 8,226,578 | B2 * | 7/2012 | Von Malmborg ........ 600/585 |
| 2005/0268725 | A1 | 12/2005 | Tulkki |

FOREIGN PATENT DOCUMENTS

| AU | 2004202152 B2 | 1/2005 |
| EP | 1 475 036 B1 | 11/2004 |
| EP | 1 616 521 B1 | 1/2006 |
| WO | WO-2005/118047 A1 | 12/2005 |

* cited by examiner

*Primary Examiner* — Max Hindenburg
*Assistant Examiner* — Jonathan M Foreman
(74) *Attorney, Agent, or Firm* — Foley & Lardner LLP

(57) ABSTRACT

Sensor guide wire for intravascular measurements of a physiological variable in a living body, comprising a core wire running along at least a part of the sensor guide wire and a sensor element arranged in a jacket in a sensor region of the sensor guide wire. The jacket is tubular and is provided with a jacket wall and a portion of the core wire that extends longitudinally along the sensor region forms part of the wall of the jacket, in order to provide more space in the jacket.

17 Claims, 3 Drawing Sheets

SECTION K-K

SECTION K-K

SECTION G-G

SECTION I-I

SENSOR GUIDE WIRE

FIELD OF THE INVENTION

The present invention relates to a sensor guide wire for intravascular measurements of a physiological variable in a living body.

BACKGROUND OF THE INVENTION

In many medical procedures, various physiological conditions present within a body cavity need to be monitored. These physiological conditions are typically physical in nature—such as pressure, temperature, rate-of-fluid flow, and provide the physician or medical technician with critical information as to the status of a patient's condition.

One device that is widely used to monitor conditions is the blood pressure sensor. The sensor is typically included in a guide wire for intravascular measurements. A blood pressure sensor senses the magnitude of a patient's blood pressure, and converts it into a representative electrical signal that is transmitted to the exterior of the patient. For most applications it is also required that the sensor is electrically energized.

Some means of signal and energy transmission is thus required, and most commonly extremely thin electrical leads are provided inside the guide wire, which itself is provided in the form of a tube (having an outer diameter of e.g. 0.35 mm), oftentimes made of stainless steel. In order to increase the bending strength of the tubular guide wire, a core wire is positioned inside the tube. The mentioned electrical leads are positioned in the space between the inner lumen wall and the core wire.

A large flexibility of the sensor guide is advantageous in that it allows the sensor guide to be introduced into small and tortuous vessels. It should, however, also be recognized that if the core wire is too flexible, it would be difficult to push the sensor guide forward into the vessels, i.e. the sensor guide must possess a certain "pushability". Furthermore, the sensor guide must be able to withstand the mechanical stress exerted on the core wire especially in sharp vessel bends.

A guide wire is disclosed in EP 1 475 036, assigned to the same assignee as the present invention, where a sensor element is positioned in a jacket in a sensor region of a distal part of the guide wire. The core wire has an enlarged section which extends through the jacket, and is provided with a recess or depression for reception of the sensor element.

The space within the jacket is thus very limited as it has to accommodate both the sensor element and the core wire. The outer diameter of the jacket is limited by the vessel geometry and the use of other intravascular catheters to about 0.35 mm, which makes it difficult to enlarge the outer diameter of the sensor guide wire.

Prior art guide wires may also be sensitive to bending as the jacket principally does not bend. The parts extending from both ends of the jacket may then be exposed to stress and a risk of damage to the guide wire arises.

The object of the present invention is to achieve a sensor guide wire that makes it possible to provide more space for sensor element(s) and accessories than in prior art sensor guide wires. A further aim of the present invention is to provide a sensor guide wire that reduces the risk of bending damages to the guide wire.

SUMMARY OF THE INVENTION

The above-mentioned object is achieved by a sensor guide wire for intravascular measurements of a physiological variable in a living body, comprising: a core wire running along at least a part of the sensor guide wire; a sensor element arranged in a jacket in a sensor region of the sensor guide wire, wherein the jacket is tubular and is provided with a jacket wall, wherein a portion of the core wire that extends longitudinally along the sensor region forms part of the wall of the jacket, in order to provide more space in the jacket.

In one embodiment, the jacket wall and the portion of the core wire (7) that extends longitudinally along the sensor region, are adapted to mate with each other. Accordingly, the mating of the jacket wall and the core wire portion result in increased space in the jacket.

According to one embodiment, the jacket wall has a longitudinal depression adapted to receive a portion of the core wire. Thus, the core wire may then be part of or even embedded in the jacket wall.

According to a further embodiment, the jacket wall has a longitudinal opening adapted to receive a portion of the core wire. Accordingly, the core wire then constitutes the jacket wall in a part of the jacket.

Preferably, the portion of the core wire that forms part of the jacket wall is recessed and/or is compressed, in order to provide more space in the jacket.

Advantageously, the portion of the core wire that forms part of the jacket wall is attached to the jacket by joints. Thus, a steady attachment of the core wire to the jacket is achieved.

In one embodiment, the sensor region is arranged with centring means adapted to place the sensor element in a central position in the jacket, in order to facilitate a correct joining of the jacket to its adjacent parts and thereby obtain a smooth envelope surface of the sensor guide wire.

Preferably, at least one end portion of the jacket or the sensing element is provided with centring means. Accordingly, the centring means are placed to get a satisfactory centring of the sensor element.

Advantageously, the centring means are in the shape of tabs protruding a small distance from the inner side of the jacket or from the sensing element, respectively, in order to control the placement of the sensing element inside the jacket.

In one embodiment, at least one part of the core wire extending longitudinally along the sensor region is shaped to function as a centring means for the sensing element. Thus, part of the core wire is utilized to arrange the sensor element in a central position.

SHORT DESCRIPTION OF THE APPENDED DRAWINGS

DETAILED DESCRIPTION OF PREFERRED EMBODIMENTS OF THE INVENTION

Figure 1:
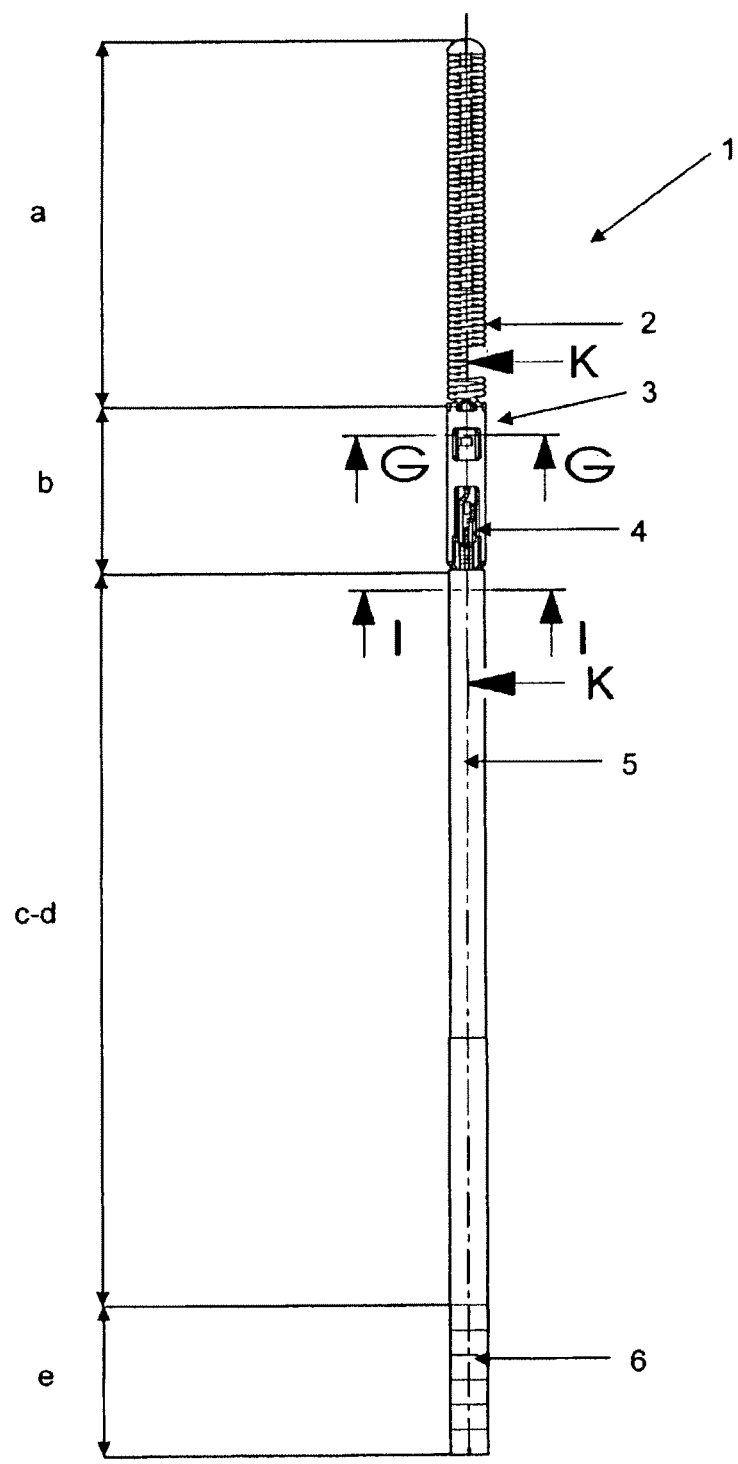
FIG. 1 shows a sensor guide wire divided in different regions.

With reference to FIG. 1, a sensor guide wire 1 for intravascular measurements according to the present invention is shown. The guide wire is divided in different regions, a-e, where region a is the most distal region and e is the most proximal region. The different regions are: a) Tip region, b) Sensor region, c) Flexible region, d) Shaft region, and e) Male connector region. In an exemplary embodiment, region a) is about 10-50 mm, region b) is about 1-5 mm, region c) is about 150-400 mm, region d) is about 1000-2000 mm and region e) is about 10-100 mm. The diameter of the sensor guide wire 1 preferably varies between 0.25-2.5 mm; for use in coronary arteries, the diameter is normally 0.35 mm.

The sensor region includes a tubular shaped jacket 3 (or sleeve), and the jacket 3 accommodates a sensor element 4. In order to power the sensor element 4 and to communicate signals representing the measured physiological variable, one or more cables or leads for transmitting signals are connected between the sensor element 4 and a male connector 6 in the male connector region. The cables are typically routed along the length of the wire.

A core wire 7 is running along at least a part of the sensor guide wire 1, and is preferably made from a metal, such as stainless steel, or a superelastic metal, e.g. Nitinol®. The mechanical properties (e.g. flexibility and strength) of the sensor guide wire 1 will mainly be determined from the material, design and dimensions of the core wire 7. Typically a sensor guide wire 1 also includes a protecting sheath or tubing 5 encompassing the core wire 7 and the above-mentioned cables.

The core wire 7 is running lengthwise inside the jacket 3, and the core wire 7 and sensor element 4 have to adapt their sizes in dependence of the space inside the jacket 3 and to each other. As the outer diameter of the jacket 3 is limited to be at most around 0.35 mm, there is no possibility to increase the outer measure of the jacket 3 to more than that.

Figure 2:
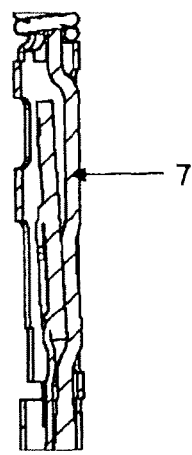
FIG. 2 is a longitudinal cross-section of the sensor region taken along K-K in FIG. 1.

The inventor of the present invention has thus realized that it is possible to increase the inner space of the jacket 3, by letting a portion of the core wire 7 that extends longitudinally along the sensor region form part of the wall of the jacket 3. The jacket 3 is tubular and has a transversely extending jacket wall. In one embodiment, the jacket wall and the portion of the core wire 7 are adapted to mate with each other. The mating of the jacket wall and the core wire portion results in increased space in the jacket, as their thickness (lateral extension) together when mating may be less than if they were separated. This is possible as they when mating may have essentially the same effect in respect of e.g. strength and protection capabilities as if they were separated. Advantageously, the jacket wall has a longitudinal depression on its inner side adapted to receive the portion of the core wire 7. FIG. 2 shows a longitudinal cross-section of the sensor region taken along K-K in FIG. 1, and shows a further advantageous embodiment, wherein the jacket wall has a longitudinal opening adapted to receive a portion of the core wire 7 that extends along the jacket 3. In this case, a side of the core wire 7 accordingly constitutes a part of the envelope surface of the sensor guide wire 1. The depression or opening in the jacket wall preferable extends along a major part of the longitudinal extension of the jacket 3.

According to one embodiment, to provide more space in the jacket 3 and to fit in the above described depression and/or opening, the portion of the core wire 7 that forms part of the jacket wall is preferably recessed.

In a further embodiment, the portion of the core wire 7 that forms part of the jacket wall is compressed. Such a recess or compression can be made by e.g. spark machining, pressing, rolling or stamping techniques.

Figure 3:
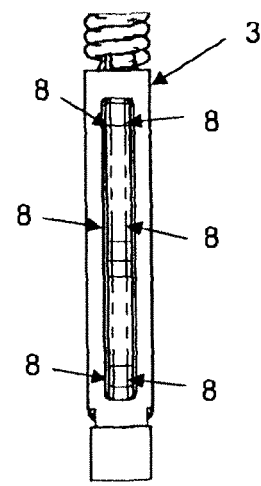
FIG. 3 shows the sensor region in detail.

The portion of the core wire 7 that forms part of the jacket wall is according to one embodiment attached to the jacket 3 by joints 8. An example of this embodiment is shown in FIG. 3. The joints 8 may be e.g. welded or soldered joints or other suitable joints. Another possible attachment arrangement is some kind of adhesive, e.g. glue.

Figure 4:
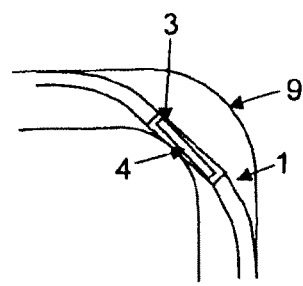
FIG. 4 illustrates the behaviour in sharp vessel bends of a sensor guide wire with a jacket.

From a mechanical (i.e. bending) point of view, the jacket 3 can be regarded as stiff. A sensor guide wire 1 has to be stiff enough to be pushed forward in a narrow and tortuous vessel and yet be flexible enough for manoeuvring in acute takeoffs. FIG. 4 is a set-up illustrating a part of a sensor guide wire 1, including a jacket 3 which is regarded as stiff, when manoeuvred through a 90-degree bend 9. The set-up is for illustrative purposes only, and demonstrates a situation that the sensor guide wire 1 may encounter. The portions distally and proximally of the jacket 3 may be exposed to wear and localized stress when the sensor guide wire 1 is manoeuvred through the bend, if the jacket 3 is not correctly joined to its adjacent parts. In one embodiment according to the invention, the sensor region is arranged with centring means adapted to place the sensor element 4 in a central position in the jacket 3. The centring means facilitates a correct joining of the jacket 3 to its adjacent parts, i.e. a proximal tube 5 and/or a coil 2. An essentially smooth envelope surface of the sensor guide wire 1 is then obtained, which reduces the risk of wear of the portions distally and proximally of the jacket 3.

Figure 5:
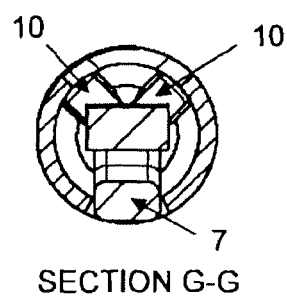
FIG. 5 is a cross-section of the sensor region taken along G-G in FIG. 1.
Figure 6:
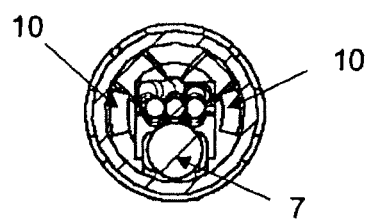
FIG. 6 is a cross-section of the sensor region taken along I-I in FIG. 1.

The centering means may, according to one embodiment, be arranged at one end portion of the jacket 3, and preferably at both ends of the jacket 3. The centring means may be in the shape of tabs 10 protruding a small distance from the inner side of the jacket 3. FIG. 5 is a cross-section of the sensor region taken along G-G in FIG. 1, which shows the centring means arranged as tabs 10 with a symmetric spacing on the inner side of a distal part of the jacket 3. FIG. 6 is a cross-section of the sensor region taken along I-I in FIG. 1, which shows protruding tabs 10 in a proximal part of the jacket 3. The tabs 10 are here positioned opposite each other on the inner side of the jacket 3. FIG. 6 also shows an embodiment where the shape of the core wire 7 is utilized as a centring means, i.e. at least one part of the core wire 7 extending longitudinally along the sensor region is shaped to function as a centring means for the sensor element 4. Other spacings and positions than the ones exemplified are of course possible. It is to be understood that it is possible to arrange the tabs 10 on the sensing element instead of on the inner side of the jacket 3, in a corresponding way as explained above.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A sensor guide wire for an intravascular measurement of a physiological variable in a living body, comprising:
    a core wire running along at least a part of the sensor guide wire;
    a cylindrical-shaped jacket comprising a tubular jacket wall, wherein the jacket wall comprises a peripheral surface extending between opposite longitudinal ends of the jacket and has a longitudinal opening, wherein the peripheral surface of the jacket wall is one external surface of the sensor guide wire, wherein a portion of the core wire that extends longitudinally along a sensor region of the sensor guide wire is disposed in the longitudinal opening of the jacket wall such that the portion of the core wire in the longitudinal opening is another external surface of the sensor guide wire, wherein the portion of the core wire in the longitudinal opening and the peripheral surface form a circumferential wall around an interior space in the sensor region; and a sensor element arranged in the interior space in the sensor region of the sensor guide wire.

2. The sensor guide wire according to claim 1, wherein the jacket comprises two additional openings in the peripheral surface.

3. The sensor guide wire according to claim 1, wherein the jacket comprises one additional opening in the peripheral surface at a distal end portion of the jacket and another additional opening in the peripheral surface at a proximal end portion of the jacket.

4. The sensor guide wire according to claim 1, wherein said portion of the core wire that forms part of the circumferential wall is bent into and out of the longitudinal opening of the jacket wall.

5. The sensor guide wire according to claim 1, wherein said portion of the core wire that forms part of the circumferential wall is compressed.

6. The sensor guide wire according to claim 1, wherein said portion of the core wire that forms part of the circumferential wall is attached to the jacket by joints.

7. The sensor guide wire according to claim 1, wherein the sensor region is arranged with spacers that place the sensor element in a central position in the jacket.

8. The sensor guide wire according to claim 7, wherein the sensor element or one of the longitudinal ends of the jacket is provided with the spacers.

9. The sensor guide wire according to claim 1, wherein the sensor region is arranged with tabs protruding a distance from an inner side of the peripheral surface of the jacket wall or from the sensor element, respectively, such that the sensor element is placed in a central position in the jacket.

10. The sensor guide wire according to claim 1, wherein at least one part of said portion of the core wire that extends longitudinally along the sensor region is shaped to place the sensor element in a central position in the jacket.

11. The sensor guide wire according to claim 1, wherein said portion of the core wire and the peripheral surface are flush with each other as continuous exterior surfaces of the sensor guide wire.

12. A sensor guide wire for an intravascular measurement of a physiological variable in a living body, comprising:
a core wire running along at least a part of the sensor guide wire;
a cylindrical-shaped jacket comprising a jacket wall, wherein the jacket wall comprises a peripheral surface extending between opposite longitudinal ends of the jacket, wherein a portion of the core wire that extends longitudinally along a sensor region of the sensor guide wire and the peripheral surface form a circumferential wall around an interior space, in the sensor region; and
a sensor element arranged in the interior space in the sensor region of the sensor guide wire,
wherein the jacket comprises one opening in the peripheral surface at a distal end portion of the jacket adjacent a cantilevered portion of the sensor element and another opening in the peripheral surface at a proximal end portion of the jacket adjacent electrical connection to the sensor element.

13. The sensor guide wire according to claim 12, wherein the peripheral surface of the jacket wall and said portion of the core wire are mated with each other so as to form the circumferential wall around the interior space.

14. The sensor guide wire according to claim 12, wherein the peripheral surface of the jacket wall has a longitudinal depression that receives said portion of the core wire.

15. The sensor guide wire according to claim 12, wherein the peripheral surface of the jacket wall has a longitudinal opening that receives said portion of the core wire.

16. A sensor guide wire for an intravascular measurement of a physiological variable in a living body, comprising:
a core wire running along at least a part of the sensor guide wire;
a cylindrical-shaped jacket comprising a jacket wall, wherein the jacket wall comprises a peripheral surface extending between opposite longitudinal ends of the jacket, wherein a portion of the core wire that extends longitudinally along a sensor region of the sensor guide wire and the peripheral surface form a circumferential wall around an interior space in the sensor region; and
a sensor element arranged in the interior space in the sensor region of the sensor guide wire,
wherein the sensor region is arranged with spacers that place the sensor element in a central position in the jacket, and
wherein the sensor region is arranged with the spacers in order to obtain a smooth envelope surface of the sensor guide wire.

17. A sensor guide wire for an intravascular measurement of a physiological variable in a living body, comprising:
a core wire running along at least a part of the sensor guide wire;
a cylindrical-shaped jacket comprising a jacket wall, wherein the jacket wall comprises a peripheral surface extending between opposite longitudinal ends of the jacket, wherein a portion of the core wire that extends longitudinally along a sensor region of the sensor guide wire and the peripheral surface form a circumferential wall around an interior space in the sensor region; and
a sensor element arranged in the interior space in the sensor region of the sensor guide wire,
wherein said portion of the core wire that extends longitudinally along the sensor region of the sensor guide wire and the peripheral surface form the circumferential wall around the interior space in the sensor region such that more space is provided in the jacket.

* * * * *